(12) United States Patent
Küntzel

(10) Patent No.: US 8,810,412 B2
(45) Date of Patent: Aug. 19, 2014

(54) DEVICE FOR WAKING UP A DRIVER AND AN OPERATOR

(75) Inventor: Klas Küntzel, Djursholm (SE)

(73) Assignee: Svenska Utvecklings Entreprenoren Susen AB, Djursholm (SE)

( * ) Notice: Subject to any disclaimer, the term of this patent is extended or adjusted under 35 U.S.C. 154(b) by 372 days.

(21) Appl. No.: 12/667,541

(22) PCT Filed: Jun. 11, 2008

(86) PCT No.: PCT/SE2008/050700
§ 371 (c)(1),
(2), (4) Date: Apr. 6, 2010

(87) PCT Pub. No.: WO2009/005444
PCT Pub. Date: Jan. 8, 2009

(65) Prior Publication Data
US 2010/0188233 A1    Jul. 29, 2010

(30) Foreign Application Priority Data

Jul. 5, 2007  (SE) .................................... 0701624-9
Apr. 21, 2008  (SE) .................................... 0800914-4

(51) Int. Cl.
*G08B 23/00*    (2006.01)
*B60K 28/06*    (2006.01)
*G08B 21/06*    (2006.01)
*A61B 5/18*    (2006.01)

(52) U.S. Cl.
CPC .............. *B60K 28/066* (2013.01); *G08B 21/06* (2013.01); *A61B 5/18* (2013.01)
USPC ... 340/575; 340/426.31; 340/439; 340/573.1; 340/576

(58) Field of Classification Search
USPC ......... 340/426.31, 438, 439, 463, 465, 573.1, 340/575, 576; 701/29, 36, 41
See application file for complete search history.

(56) References Cited

U.S. PATENT DOCUMENTS 6,087,943 A * 7/2000 Bailey ........................... 340/576
6,218,947 B1 * 4/2001 Sutherland ................... 340/576

(Continued)

FOREIGN PATENT DOCUMENTS

DE    202004001832 U    5/2004
EP    0 856 432 A2      8/1998
WO    WO 01/16910       3/2001

OTHER PUBLICATIONS

International Search Report, dated Oct. 21, 2008, from corresponding PCT application.

*Primary Examiner* — George Bugg
*Assistant Examiner* — Sharmin Akhter
(74) *Attorney, Agent, or Firm* — Young & Thompson

(57) ABSTRACT

An arrangement to awaken a sleeping driver or operator of a vehicle, a vessel, an aeroplane or any other system that is controlled by a person, includes a detection part that is arranged to measure movements of a control element that belongs to the vehicle with which control element the driver has hand contact, a calculation circuit arranged to compare movements of the control element over time, and an alarm part arranged to produce vibrations in the control element. The calculation circuit is arranged to activate the alarm part when no movement of the control element has occurred during a pre-determined period, which pre-determined period indicates that the driver has fallen asleep, and in that all the parts are mounted on or are integrated with the control element.

18 Claims, 6 Drawing Sheets

(56) References Cited

U.S. PATENT DOCUMENTS

| | | | |
|---|---|---|---|
| 6,236,306 B1 * | 5/2001 | Liebelt | 340/407.1 |
| 6,313,749 B1 * | 11/2001 | Horne et al. | 340/575 |
| 6,575,902 B1 | 6/2003 | Burton | |
| 6,920,234 B1 * | 7/2005 | Koenig et al. | 382/103 |
| 7,019,653 B2 | 3/2006 | Benedict | |
| 7,427,924 B2 * | 9/2008 | Ferrone et al. | 340/576 |
| 7,696,863 B2 * | 4/2010 | Lucas et al. | 340/435 |
| 7,961,085 B2 * | 6/2011 | Almqvist et al. | 340/439 |
| 2003/0210150 A1 * | 11/2003 | Benedict | 340/575 |
| 2005/0021204 A1 * | 1/2005 | Kudo | 701/36 |
| 2005/0151624 A1 * | 7/2005 | Qualich et al. | 340/5.72 |
| 2011/0082614 A1 * | 4/2011 | Tichy et al. | 701/29 |

\* cited by examiner

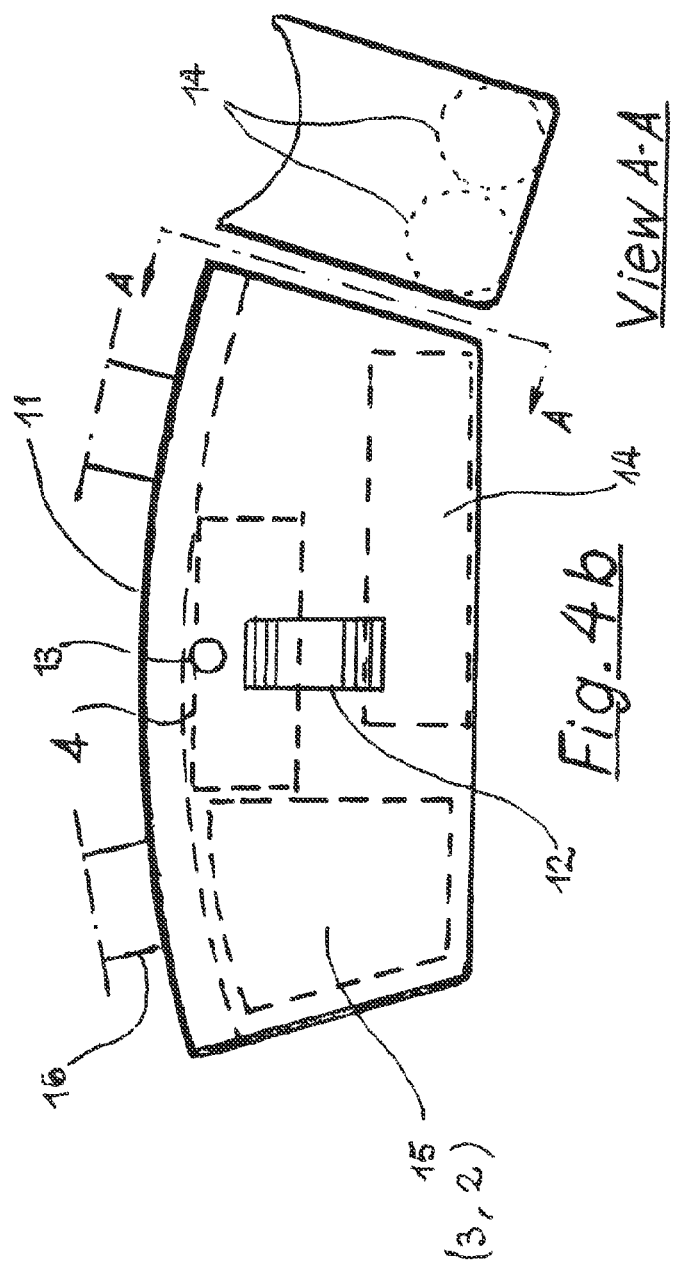

DEVICE FOR WAKING UP A DRIVER AND AN OPERATOR

The present invention relates primarily to active safety systems in motor vehicles, particularly such systems whose primary task is that of preventing traffic accidents caused by the driver falling asleep while driving. Such systems may contain two main tasks: that of detecting the degree of tiredness of the driver, and that of warning or waking the driver if this becomes necessary. The present system is limited to detecting that the driver has fallen asleep and subsequently waking the driver. The technical area as such extends beyond motor vehicles, and the invention can be applied also within other systems that are operated by a person.

A number of different methods and arrangements in motor vehicles for detecting the degree of tiredness of the driver have become known. These are based not only on sensors of different types in order to measure physiological properties of the driver, movements of the vehicle, movements of the steering wheel, or other parameters that reflect the condition or behaviour of the driver or the vehicle; but also on various calculations, based on the data that has been collected, and on statistical data and selected algorithms. The following belong to known, described and also realised sensor data: the results from camera studies of the eyes and eyelid movements of the driver, the force of the hands on the steering wheel, camera data from lateral motion of the vehicles across lane markers, data from sensors of lateral acceleration in the vehicle, and other data. Systems have been described that include the computer processing of algorithms and statistical correlations for the calculation of the degree of tiredness and lack of attention of the driver, based on measured sensor data and stored statistical data, and on pre-programmed threshold values for alarms of different intensities.

A normal disadvantage of systems intended to detect the degree of human tiredness is that of individual differences. It is known that all muscle movement that is consciously controlled in humans ceases when asleep, independently of individual differences, and this observation is used by the present patent.

Acoustic, visual and haptive signals are known methods of warning or awakening the driver, where the acoustic methods include buzzers, alarms, and recorded warnings; the visual methods include lamps and various types of flashing light, and also indicator instruments; and the haptive methods include vibrations of the driver's seat, seat belt or steering wheel. It is known that a person can no longer interpret visual impressions once asleep. It is also known that both acoustic and haptive signals can be experienced by a person, at least during the early phase of sleep. Acoustic signals may be difficult to experience as a result of poor hearing or other sounds in a vehicle, while correctly designed haptive signals, as described here, are directly experienced by the sleeping person.

One characteristic property of all described systems is that they contain one or more sensors or detectors installed at some location in the vehicle, connected to electronic circuits installed in the vehicle and connected to the one or several alarm arrangements or instruments, or both arrangements and instruments, whereby data is transferred between the system components in a known manner, often using cables.

Different known methods of arranging mechanical vibrators as alarm in a vehicle steering wheel are described in patent number EP 0 856 432, and include previously known piezoelectric vibrators, imbalance motors, and oscillating linear electromechanical vibrators.

A method is described in the PCT application SE2007/050280 for alarming a driver of a vehicle whose behaviour at the steering wheel leads to deficiencies in control and where mechanical vibrators in the steering wheel are used in such a manner that the vibrations that have been instigated by the alarm have a nature that has been specially selected, particularly with respect to their frequencies, but also with respect to their durations, pauses and amplitudes, all of this being adapted to the physiological ability of a person to experience sensory input in the hand and fingers in the most effective and rapid manner.

The present invention uses mechanical vibrators in the steering wheel in the same manner, preferably with, but not limited to, those of a vibratory nature according to Patent SE 529 656, whereby the complete security system, including the detection of falling asleep and alarm for the driver, has been installed within or on the control means.

The problem of drivers of vehicles who fall asleep is current, and it has been assigned great significance in modern motor traffic, since the statistics that are available suggest that up to 30% of all fatal accidents in traffic are caused by inattention at the steering wheel and, in the majority of cases, falling asleep at the steering wheel.

Current vehicles lack, with a few exceptions, a solution and previously published solutions often demonstrate a complicated structure with installation of system components at different locations in the vehicle, which entails risks associated with cabling, contamination of camera lenses, interruptions in signal transfer or other disturbances in function, these risks may be attributed to conditions associated with the driver, with system components, or with the electronic system. It is one desire that a safety system in motor vehicles demonstrate a high reliability.

The present invention offers a simple and rapidly operating solution with a local and concentrated design, which will give a reliable, easily monitored function, and long life.

An arrangement according to the invention can in one embodiment be mounted as an addition in an existing motor vehicle through the fixing of the control means.

The present invention thus relates to an arrangement to awaken a sleeping driver or operator of a vehicle, a vessel, an aeroplane or any other system that is controlled by a person, comprising a detection part arranged to measure the movement of a control means that belongs to the vehicle with which control means the driver has hand contact, a calculation circuit arranged to compare the movement of the control means over time, and an alarm part arranged to produce vibrations in the control means, and it is characterised in that the calculation circuit is arranged to activate the alarm part when no movement of the control means has occurred during a pre-determined period, which pre-determined period indicates that the driver has fallen asleep, and in that all the said parts are mounted on or are integrated with the said control means.

The two tasks, that of detecting that the driver has fallen asleep and that of awakening the driver, have been united in the present invention in the steering wheel of the vehicle, which is the mobile component in the controlled vehicle that is in continuous contact with the driver and that determines the lateral motion of the vehicle.

A system according to the invention detects the rotation movements of the steering wheel around the steering wheel shaft using a detection part that comprises a movement detector in the steering wheel or on the steering wheel. The sensor can be realised using prior art technology following various principles. The period since the most recent steering wheel movement is calculated and it can constitute an indication that the driver has fallen asleep.

According to one preferred embodiment, the said detection part comprises one or several accelerometers arranged to detect accelerations in a direction that is tangential to the steering wheel.

According to another embodiment, the said detection part comprises an angle sensor arranged to detect changes in the angle between the steering wheel and a fixed part of the vehicle.

A system according to the invention contains at least one electronic circuit, preferably mounted inside or on the steering wheel, that calculates the time that has elapsed since the most recent steering wheel movement on the basis of the said measured and calculated data, and compares these data with at least one threshold value, stored in the electronic circuit, which is designed to raise an alarm according to stored conditions.

A system according to the invention contains, further, at least one vibrator known per se in or on the steering wheel, designed such that it is able to generate such vibrations in the surface of the steering wheel that they are experienced by the hands of the driver, when they are resting on the steering wheel, in a comfortable but effective manner. The vibrator is of a suitable known type.

According to one preferred embodiment, the said control means is constituted by a steering wheel and the alarm part is arranged to cause the said vibrations in the surfaces of the steering wheel against which the hands of the driver rest, and in that the vibrations act in a direction that is perpendicular to the outer surface of the steering wheel.

A system according to the invention is characterised in that all of the said components of the system may be mounted on or inside of a steering wheel and that they can be fed with a low-voltage direct current, preferably with the normal voltage of the vehicle, which may be 12 or 24 volts, led up into the steering wheel, or that they can be fed with batteries of a suitable voltage mounted on the steering wheel.

In one preferred embodiment of the invention, the electronic circuit has been designed such that it switches off an alarm that has been initiated as soon as the system detects a rotation movement in the steering wheel.

In an extended embodiment, the electronic circuit has been designed such that it is able to supply signals to other active safety systems in the vehicle in the case in which the steering wheel movements cannot be detected within a certain period after the raising of the alarm. Such other active safety systems in the vehicle have the task of reducing the risk of, and the consequences of, an imminent traffic accident.

The obvious advantage of the invention is that the system for warning of a driver falling asleep, including the detection part in it entirety, is designed such that it can be installed in or on the control means, which in the case of a vehicle is constituted by the steering wheel, while at the same time the detection of falling asleep, as it has been designed, is independent of an individual. This automatically entails integration and simplicity of the arrangement, with fixed and fully protected signals and power feeds. An arrangement according to the invention can thus be miniaturised to become a very compact unit for detection and control, using short conductors. The total cost of the system will in this way be low. It is not possible to solve the task in a simpler, more rapid or safer manner, something that is highly is desirable in the control of motor vehicles.

FIG. 4b shows examples of an external design of such a mountable arrangement according to the invention.

The principle of the invention is to concentrate in the control means not only the arrangements for the detection of falling asleep when controlling a dynamic system, but also the arrangements to awaken the person who is controlling the system. This principle is described here as an application in motor vehicles, where the control means is the vehicle steering wheel.

Figure 1:
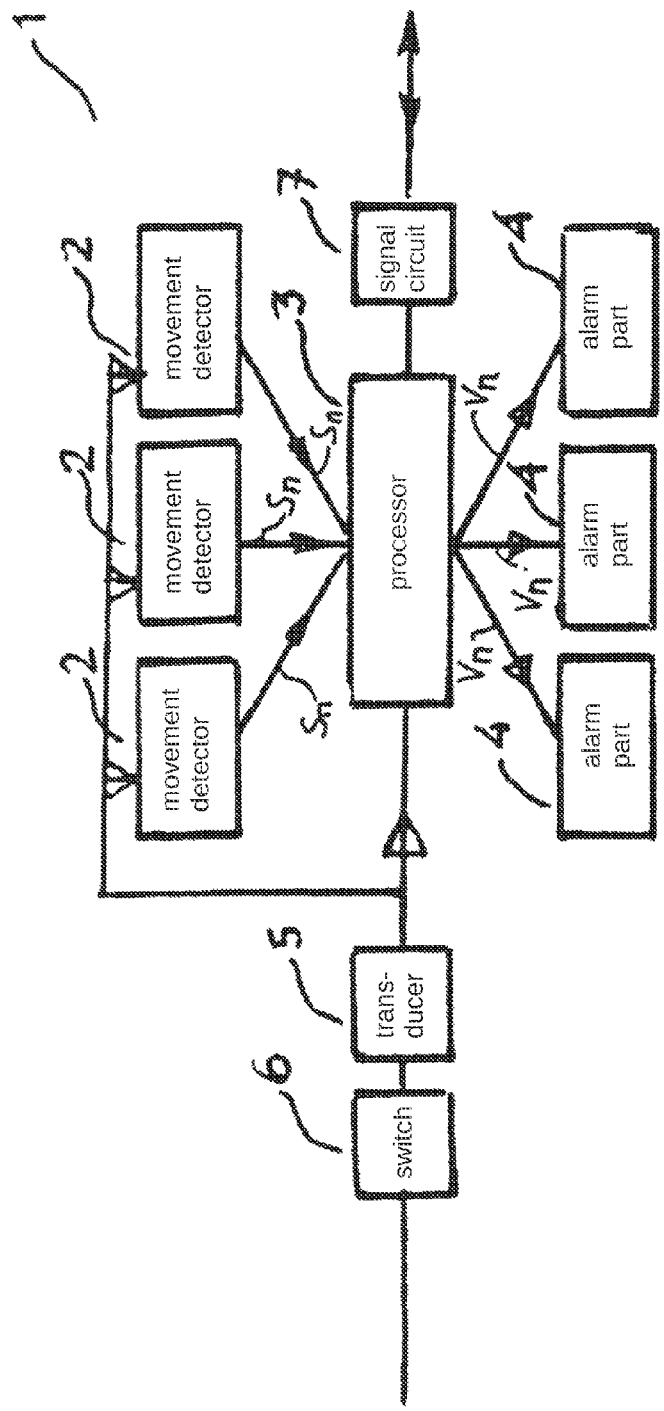
FIG. 1 shows an example of an embodiment of the invention in a functional block diagram.

FIG. 1 shows the functional components of the arrangement with the following reference numbers:

1 denotes the control means in block diagram form.
2 denotes movement detectors, including the signal processing.
3 denotes a processor with electronic control circuits.
4 denotes electromechanical vibrators.
5 denotes transducers.
6 denotes switches.
7 denotes signalling circuits or cabling.

With reference to FIG. 1, the function of the arrangement is essentially as follows:

The movement detector 2 issues a signal $s_n$ to the calculation part 3 at each detected steering wheel movement during motion of the vehicle. The time that has passed since the most recent steering wheel movement is summed in the calculation part 3, and the summation register is set to zero on each incoming steering wheel movement $s_n$ and time registration recommences from zero. At least one threshold value $t_n$ has been pre-programmed into the calculation part 3.

If the time summation in the summation register should reach the threshold value $t_n$, alarm voltages $v_n$ are issued to the alarm part 4.

If the reaction of the driver to the steering wheel vibration that is caused by the alarm part 4 is to move the steering wheel, this is registered in the movement detector 2, whose subsequent signal $s_n$ to the calculation part sets the summation register to zero, which automatically interrupts the alarm voltages $v_n$ sent to the alarm part 4.

If there is no reaction of the driver to the steering wheel vibration that is caused by the alarm part 4 for a certain pre-programmed period after the alarm has been raised, the system may be designed such that it communicates using known technology with other active safety systems in the vehicle through a signal circuit 7 or directly through cabling. The signalling process in 7 may, for example, use Bluetooth technology.

A system for warning when a driver falls asleep according to the invention is to be switched on and switched off with a switch 6. FIG. 1 shows the invention in one embodiment, whereby the switching on and switching off of the arrangement can take place either with a manually operated switch 6 or with an automatic switch 6 that is controlled by the movements of the vehicle. It is furthermore a condition that the switch is placed under voltage only when the ignition key of the vehicle has been activated.

The power required for the voltage desired for the various parts of the arrangement can be converted as required in the transducer 5 of the arrangement.

Figure 2:
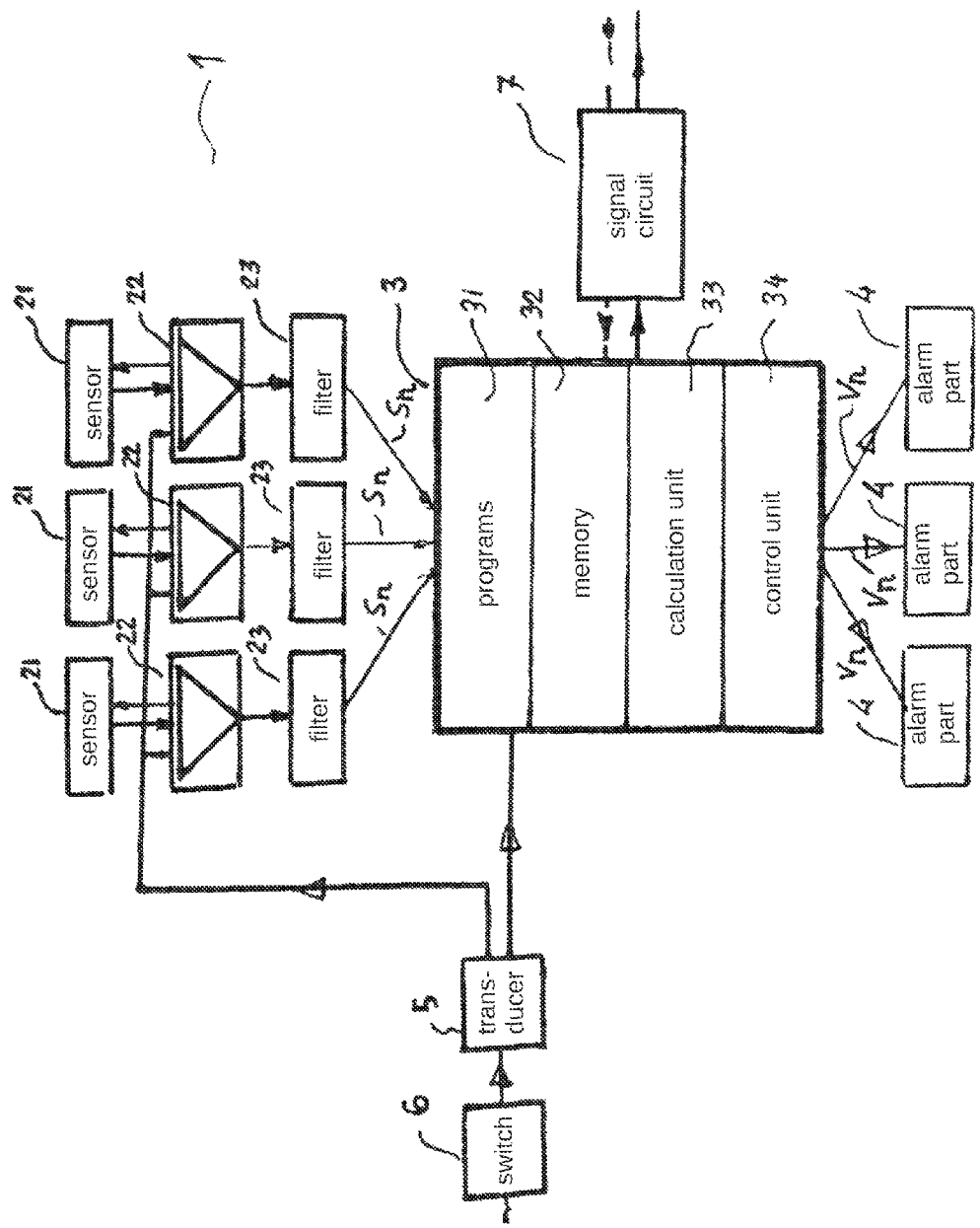
FIG. 2 shows a corresponding functional summary connection diagram for the same embodiment of the invention.

FIG. 2 shows in more detail the functional parts of an arrangement according to the invention, where:
- 21 denotes movement sensors, such as accelerometers
- 22 denotes amplifiers
- 23 denotes filters
- 31 denotes programs
- 32 denotes memory
- 33 denotes a calculation unit
- 34 denotes a control unit.

The invention uses prior art technology for detecting motion of the steering wheel with at least one sensor 21, for example an accelerometer, in the control means. It may be suitable in order to eliminate the influence of motion of the vehicle that the arrangement contains several accelerometers, such as three accelerometers 21, the detected values of which can be converted in the filter 23 and compared for their agreement in terms of the angular motion $s_n=s_{1,2,3}$ of the steering wheel.

The processor 3 with its control circuits 34 stores in its memory 32 a program 31, which is processed in a calculation unit 33, where conditions for raising an alarm are calculated, based on the input data received and on elapsed time.

The unit 33 in its simplest form calculates elapsed time since the most recent steering wheel movement $s_n$ and compares this time with a pre-programmed threshold value in the memory 32. The arrangement and the algorithm in a further version may use other input data, such as the speed of the vehicle, a process that can take place through communication with the CAN bus of the vehicle through wires or through the signal circuit 7. The distance travelled since the most recent steering wheel movement can in this case be used as threshold value for the raising of an alarm.

New reference symbols in FIGS. 3a, 3b, 4a and 4b are:
- x-x constitutes a horizontal line through the steering wheel ring when at its neutral position (the wheels directed in the longitudinal direction of the vehicle).
- y-y a line that is perpendicular to x-x and that lies in the plane of the steering wheel ring.
- 8 denotes a unit that contains sensors and electronic circuits according to the arrangement
- 9 denotes the supporting metal spokes of the spokes of the steering wheel.
- 10 denotes the supporting metal ring of the steering wheel ring.
- 11 denotes an arrangement according to the invention for supplementary mounting onto the steering wheel of a vehicle.
- 12 denotes a manual switch.
- 13 denotes a light-emitting diode.
- 14 denotes batteries that can be exchanged.
- 15 denotes the position of a printed circuit containing the relevant electronic components, including an accelerometer.

Figure 3A:
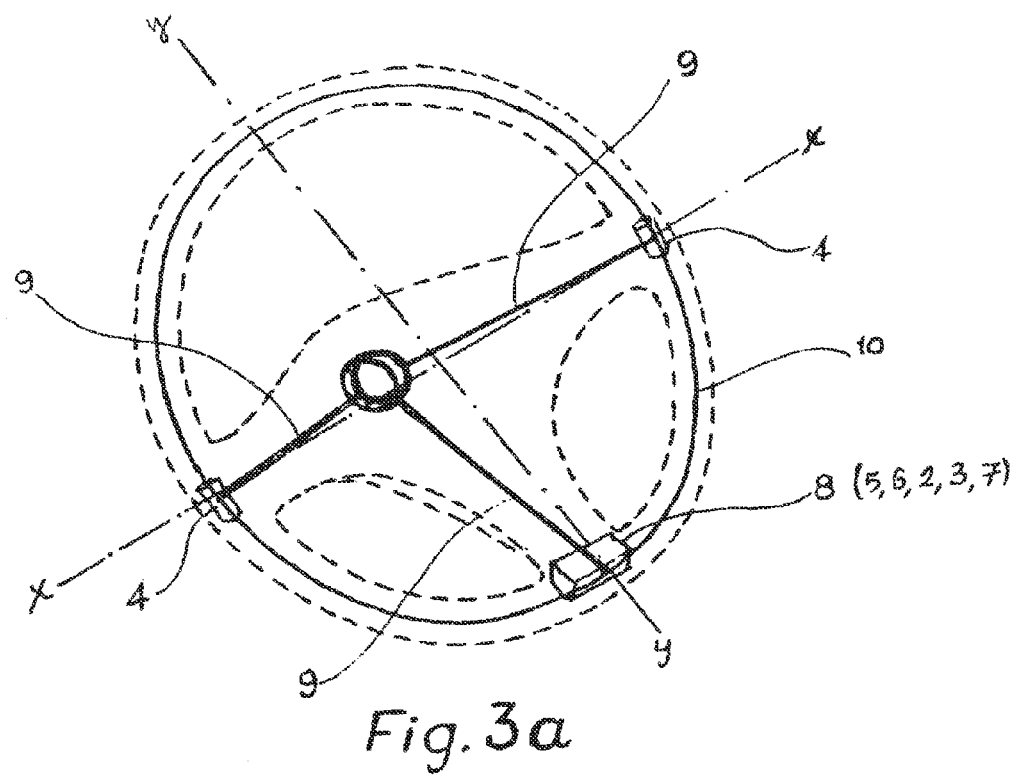
FIG. 3a shows a three-dimensional sketch of a vehicle steering wheel on which an arrangement of one embodiment of the invention has been installed.

FIG. 3a shows a three-dimensional sketch of an arrangement according to the invention in a basic design with only one accelerometer 21, installed in an arrangement in the steering wheel ring such that its greatest sensitivity acts in a direction that is tangential to the steering wheel ring and preferably such that it is located in the vicinity of a line y-y in the plane of the steering wheel ring and perpendicular to a horizontal line x-x in the same plane. The location has been selected considering the fact that most cases of a driver falling asleep while driving can be expected to take place when the steering wheel is close to its neutral position, when the front wheels are directed straight ahead, whereby the sensitivity of the accelerometer is greatest in the lateral direction with respect to movements both of the steering wheel and of the vehicle. All electronic circuits can in this embodiment be contained within the same unit 8, which may be miniaturised and contain, in addition to the accelerometer 21 the associated circuits 22, 23 and the processor 3, including electronic control circuits 34 for feeding vibrators 4. The embodiment in FIG. 3a comprises two vibrators 4, which may be encapsulated imbalance motors, operating at the same frequency or at two specially selected different frequencies and that are preferably mounted in fixed mechanical contact with the spokes 9 of the steering wheel or the metal structure 10 of the steering wheel ring.

Figure 3B:
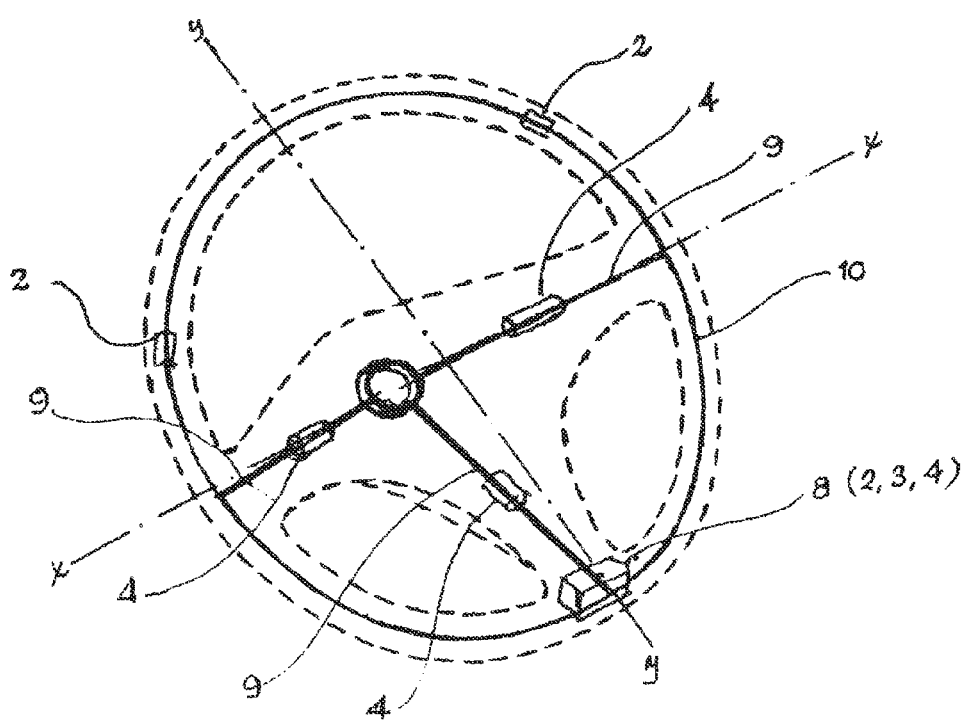
FIG. 3b shows in the same way examples of a second embodiment.

FIG. 3b shows examples of a further embodiment of the invention—one that uses several accelerometers 21 distributed at different locations around the periphery of the steering wheel ring, such that accelerations of angle in the steering wheel ring can be distinguished from accelerations of the vehicle in different directions. Three accelerometers 21 at an approximate angular separation of 120° are shown in the drawing. Other electronic circuits can be located at a suitable location in a unit 8 and the example shows three vibrators 4 each located in a separate spoke 9 of the supporting structure of the steering wheel.

Figure 4A:
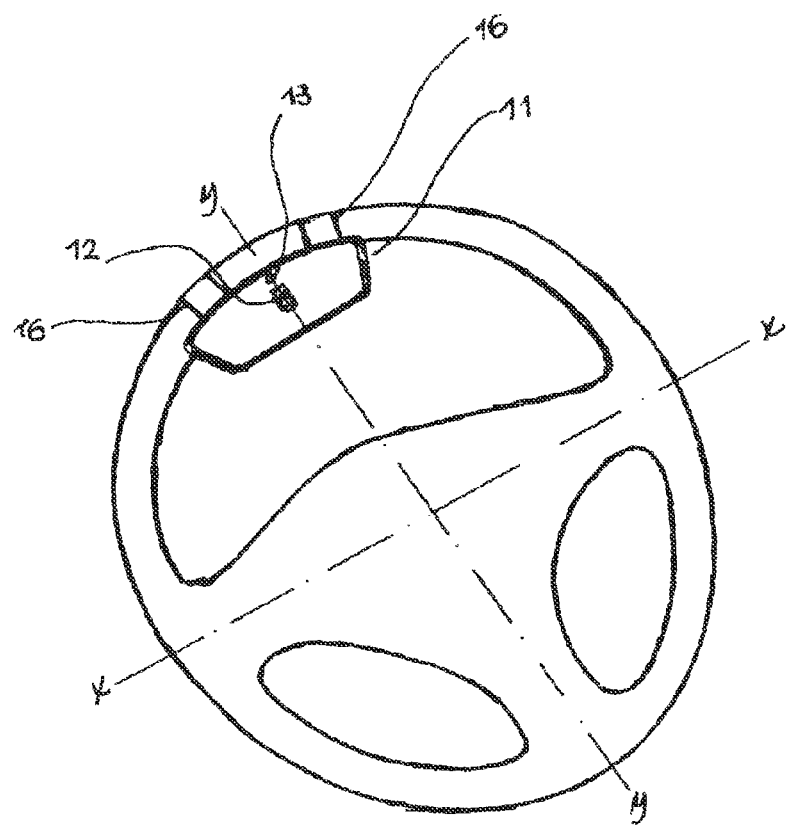
FIG. 4a shows a three-dimensional sketch with examples of how an arrangement according to the invention may be mounted as additional equipment on a steering wheel in motor vehicles.

FIG. 4a shows an arrangement 11 according to the invention, mechanically fixed attached to the steering wheel ring using prior art technology, for example using plastic or metal strips 16. The arrangement 11 contains at least one accelerometer 21 arranged with its greatest sensitivity in a direction that is tangential to the steering wheel ring, the processor 3 with electronic control circuits 34 for feeding vibrators, at least one vibrator 4 and holders for suitable batteries, such as batteries of type AA. It is assumed that it is appropriate that the arrangement be provided with a manual switch 12, and it is also a good idea if it is provided with a low-consumption light-emitting diode 13 or similar that indicates when the arrangement is functioning. The arrangement may contain also an automatic switch that is controlled by movements of the vehicle.

FIG. 4b shows one possible appearance of a mountable arrangement 11 designed to be mounted as shown in FIG. 4a on the inner surface of the upper side of the steering wheel ring according to the invention. The arrangement 11 contains, in addition to batteries 14 that can be exchanged, at least one vibrator 4, which may be an imbalance motor, miniaturised electronic circuits 15, comprising all of the circuits required, such as a processor 3 with electronic control circuits 34 and a miniaturised accelerometer 21 with its associated circuits 22, 23. FIG. 4b shows also a manual switch 12, and a light-emitting diode 13 that indicates that the arrangement is functioning.

The present invention has been described in various embodiments with reference to FIGS. 1-4, intended to provide examples of the principle of the invention—that of enclosing the complete function of an active monitoring system in the actual steering wheel or as an accessory to the actual steering wheel in order to prevent, principally, traffic accidents caused by the driver falling asleep at the steering wheel. The invention, however, is not limited to embodiments described here and in the drawings since it can be varied with prior art technology within the scope of the attached patent claims.

The invention claimed is:

1. An arrangement to awaken a sleeping operator of a vehicle that is controlled by a person, comprising:
   a detection part that is configured to measure movements of a steering control device that belongs to the vehicle to which the driver is to have hand contact for controlling steerage of the vehicle, the detection part comprising a movement detector in or on the control device;

a calculation circuit configured to compare movements of the control device over time; and an alarm part configured to produce vibrations in surfaces of the control device that are configured for contact with hands of the operator, wherein the calculation circuit is configured to activate the alarm part when no movement of the control device has occurred during a pre-determined period sufficient to indicate that the driver has fallen asleep, wherein all of said detection part, said calculation circuit, and said alarm part are mounted on or are integrated with the control device, wherein the calculation circuit is configured to deactivate the alarm arrangement upon detection of a movement of the control device while the alarm system is activated, and wherein the alarm part is configured to produce vibrations in a direction that is perpendicular to an outer surface of the control device upon which hands of the operator rest during operation.

2. The arrangement according to claim 1, wherein the control device is a steering wheel.

3. The arrangement according to claim 1, wherein the detection part comprises one or several accelerometers configured to detect accelerations in a direction that is tangential to the control device.

4. The arrangement according to claim 1, wherein the detection part comprises an angle sensor configured to detect changes in an angle between the control device and a fixed part of the vehicle.

5. The arrangement according to claim 2, wherein an entirety of the arrangement is configured to be mounted inside the steering wheel.

6. The arrangement according to claim 2, wherein the detection part comprises one or several accelerometers configured to detect accelerations in a direction that is tangential to the steering wheel.

7. The arrangement according to claim 2, wherein the detection part comprises an angle sensor configured to detect changes in an angle between the steering wheel and a fixed part of the vehicle.

8. The arrangement according to claim 3, wherein the detection part comprises an angle sensor configured to detect changes in an angle between the control device and a fixed part of the vehicle.

9. The arrangement according to claim 2, wherein an entirety of the arrangement is configured to be mounted on the steering wheel.

10. The arrangement according to claim 3, wherein an entirety of the arrangement is configured to be mounted on the control device.

11. The arrangement according to claim 4, wherein an entirety of the arrangement is configured to be mounted in the control device.

12. The arrangement according to claim 1, wherein the control device is a hand-operated steering control for the vehicle, and all of said detection part, said calculation circuit, and said alarm part are located within one or more spaces inside said steering control.

13. The arrangement according to claim 1, wherein the alarm part is mounted inside the control device and is configured to produce vibrations in a direction that is perpendicular to an outer surface of the control upon which hands of the operator rest during operation.

14. The arrangement according to claim 13, wherein the calculation circuit is configured to deactivate the alarm arrangement upon detection of a movement of the control device that occurs while the alarm system is activated.

15. The arrangement according to claim 1, wherein, in an event where the alarm part remains activated for another pre-determined period, the calculation circuit communicates with other active safety systems in the vehicle.

16. The arrangement according to claim 15, wherein the calculation circuit communicates with said other active safety systems in the vehicle via wireless communications.

17. The arrangement according to claim 1, wherein the alarm part comprises two vibration devices mounted in fixed mechanical contact with different spokes of the control device.

18. The arrangement according to claim 17, wherein the two vibration devices operate at different frequencies.

* * * * *